United States Patent [19]

Norris et al.

[11] Patent Number: 4,826,763

[45] Date of Patent: May 2, 1989

[54] PROCESS FOR PREPARING GLUCAGON OR FRAGMENTS OR DERIVATIVES THEREOF IN YEAST

[75] Inventors: Kjeld Norris, Hellerup; Lars Thim, Gentofte; Fanny Norris, Hellerup; Mogens T. Hansen, Olstykke; Alister J. Moody, Holte, all of Denmark

[73] Assignee: Novo Industri A/S, Bagsvaerd, Denmark

[21] Appl. No.: 820,144

[22] Filed: Jan. 21, 1986

[30] Foreign Application Priority Data

Jan. 22, 1985 [DK] Denmark ............................ 278/85

[51] Int. Cl.$^4$ .................. C12P 21/00; C12P 21/02; C12N 5/00; C12N 15/00
[52] U.S. Cl. .................................. 435/68; 435/70; 435/254; 435/255; 435/256; 435/320; 435/172.3; 935/13; 935/28; 935/48; 935/69
[58] Field of Search ............... 435/68, 70, 172.3, 255, 435/256, 320, 254; 514/12, 13; 935/13, 28, 47, 48, 56, 69; 530/324, 326, 308

[56] References Cited

U.S. PATENT DOCUMENTS

| 4,401,759 | 8/1983 | Rubin et al. | 435/91 |
|---|---|---|---|
| 4,546,082 | 10/1985 | Kurjan et al. | 435/68 |
| 4,598,065 | 7/1986 | Lündt | 514/12 |

OTHER PUBLICATIONS

Kurjan et al., Cell vol. 30 1982, pp. 933–943.
Lund et al., *PNC Natl. Acad. Sci.* Jan. 1982 vol. 79 pp. 345–344 "Pancreatic Preproglucagon cDNA contains two glucagon-related coding Sequences arranged in tandem".
Cabezon et al. *PNC Natl. Acad., Sci.* vol. 81 pp. 6544–6598 Nov. 1984 "Expression of human α, -antitrypsin cDNA on the yeast *Succharomyces cerevisiae*".
Ztakura et al., *Science* vol. 198 vol. No. 1056–1063.

*Primary Examiner*—Robin Teskin
*Attorney, Agent, or Firm*—Morris Fidelman; Franklin D. Wolffe

[57] ABSTRACT

Glucagon or fragments or derivatives thereof are prepared by cultivation of a yeast strain transformed with a replicable expression vehicle comprising a gene encoding the expression of such products. Synthetic genes encoding glucagon or derivatives thereof have been constructed. Also provided are replicable expression vehicles comprising a replication system for providing stable maintenance in yeast and a DNA-sequence encoding glucagon or fragments or derivatives thereof and transformant yeast strains containing such expression vehicles.

2 Claims, 7 Drawing Sheets

FIG. 7
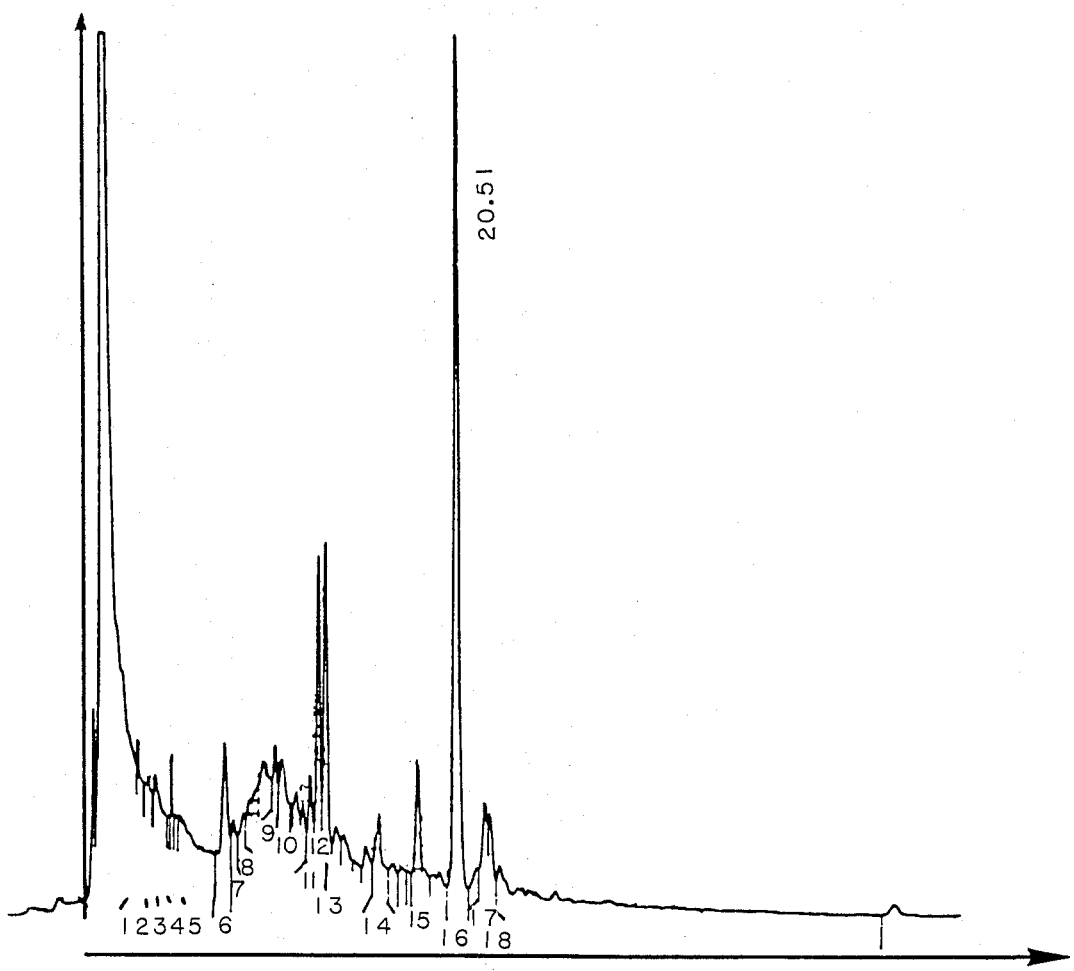
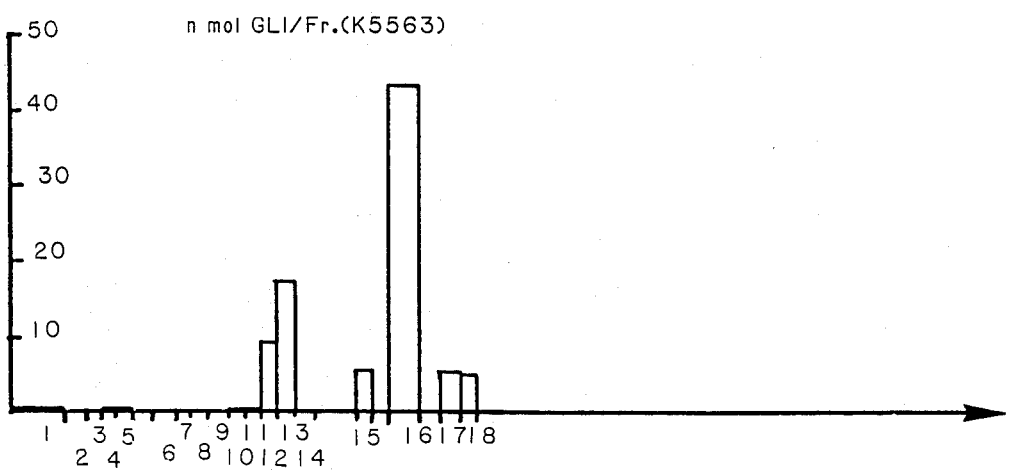

4,826,763

PROCESS FOR PREPARING GLUCAGON OR FRAGMENTS OR DERIVATIVES THEREOF IN YEAST

FIELD OF THE INVENTION

This invention relates to a process for producing glucagon or fragments or derivatives thereof in yeast, synthetic genes encoding glucagon or fragments or derivatives thereof, corresponding expression vehicles and transformed yeast strains.

DESCRIPTION OF THE BACKGROUND ART

Glucagon is a polypeptide hormone, secreted by the α-cells of the pancreatic islets of Langerhans. It is a single-chain polypeptide consisting of 29 amino acids in the following sequence:

His—Ser—Gln—Gly—Thr—Phe—Thr—Ser—Asp—Tyr— (I)
—Ser—Lys—Tyr—Leu—Asp—Ser—Arg—Arg—Ala—Gln—
—Asp—Phe—Val—Gln—Trp—Leu—Met—Asn—Thr

Glucagon is used for the treatment of hypoglycemia due to its metabolic effects. Glucagon also exerts a spasmolytic effect on smooth muscle and an inhibitory effect on gastric secretion.

Glucagon is isolated from pancreas extracts. The extraction of glucagon from pancreas from slaughtered animals is a complicated process and requires large amounts of pancreas. As glucagon is furthermore sensitive to proteolytic degradation the product from the extraction of pancreas is inhomogenous and only about ¼ of the glucagon content of pancreas is obtained.

From EP-patent application No. 81302978 (see also Ser. No. 279,153 filed June 30, 1981 now U.S. Pat. No. 4,598,065) fragments or derivatives of glucagon are known with the following general formula:

$R^1$-$R^2$ (II)

wherein $R^1$ represents His-Ser-Gln-Gly-Thr-Phe-Thr-Ser-Asp-Tyr-Ser-Lys-Tyr-Leu-Asp-Ser-Arg-Arg-Ala-Gln-Asp, and $R^2$ represents OH, the peptide chains -Phe-Val-Gln-Trp-Leu or -Met-Asn-Thr or a corresponding peptide chain which is identical with the two last-mentioned peptide chains with the proviso that one or more of the amino acid(s) of the said two last-mentioned peptide chains has/have been omitted.

The compounds of formula (II) possess a similar spasmolytic effect and a similar inhibitory effect on gastric acid secretion as that of glucagon, but show no or minor, negligible metabolic effect. Hence, compounds of formula (II) are considered superior to glucagon when only a spasmolytic effect or an inhibition of gastric acid secretion is desired.

The compounds of formula (II) can be prepared either from natural glucagon or by the rather troublesome methods which are generally known in peptide synthesis. A preferred compound of formula (II) is glucagon (1-21).

In this specification numbers in a paranthesis after glucagon indicate the number of amino acids. Natural glucagon contains 29 amino acids and is referred to as glucagon(1-29) (or just glucagon). Glucagon(1-21) contains the first 21 amino acid residues of naturally occurring glucagon and so on.

The object of the present invention is to provide a more profitable commercial process for the preparation of glucagon or fragments or derivatives thereof by use of recombinant DNA techniques.

SUMMARY OF THE INVENTION

The invention is based on the surprising discovery that glucagon and a derivative thereof (glucagon(1-21)) can be expressed in high yields as a homogeneous material in the supernatant from the cultivation of a yeast strain transformed with a DNA-sequences encoding such products.

According to a first aspect of the present invention there is provided a method for producing high yields of glucagon or fragments or derivatives thereof in yeast by cultivation of a yeast strain containing replicable expression vehicle comprising a gene encoding glucagon or fragments or derivatives thereof in a suitable nutrient medium followed by recovery of the expressed product from the culture medium.

The gene encoding glucagon(1-29) may be a synthetic gene or may be derived from a cDNA clone of glucagon or from a genomic clone of glucagon.

Preferably glucagon or fragments or derivatives thereof are prepared by insertion of a synthetic gene encoding the desired product in a suitable yeast DNA-expression vehicle, transformation of a suitable yeast host strain with the expression vehicle and cultivation of the transformed microorganism whereafter the expressed product is recovered from the culture broth.

According to a second aspect of the present invention a DNA-sequence is provided comprising a synthetic gene encoding the expression of glucagon or fragments or derivatives thereof in yeast.

According to a third aspect of the present invention there is provided a replicable expression vehicle comprising a replication system for providing stable maintenance in yeast and a DNA-sequence encoding glucagon or fragments or derivatives thereof.

According to a fourth aspect of the present invention there is provided a transformed yeast strain containing an replicable expression vehicle capable of expressing glucagon or fragments or derivatives thereof in yeast.

By transformation of a suitable yeast host with the above expression vehicle high yields of the desired product was produced. Surprisingly the glucagon or the glucagon fragments formed were very homogeneous and no cleavage at the dibasic amino acid sequence Arg-Arg at position 17 and 18 of glucagon was observed by enzymes produced by the yeast during cultivation. This is highly surprising as yeast is known to produce trypsin-like endopeptidase enzymes which specifically cleave at the site of such pair of basic amino acids.

DESCRIPTION OF THE DRAWINGS

The invention will be further described with reference to the accompanying drawings in which FIG. 7 shows a preparative fractionation of the concentrated DEAE breakthrough.

DESCRIPTION OF THE PREFERRED EMBODIMENTS

Figure 1:
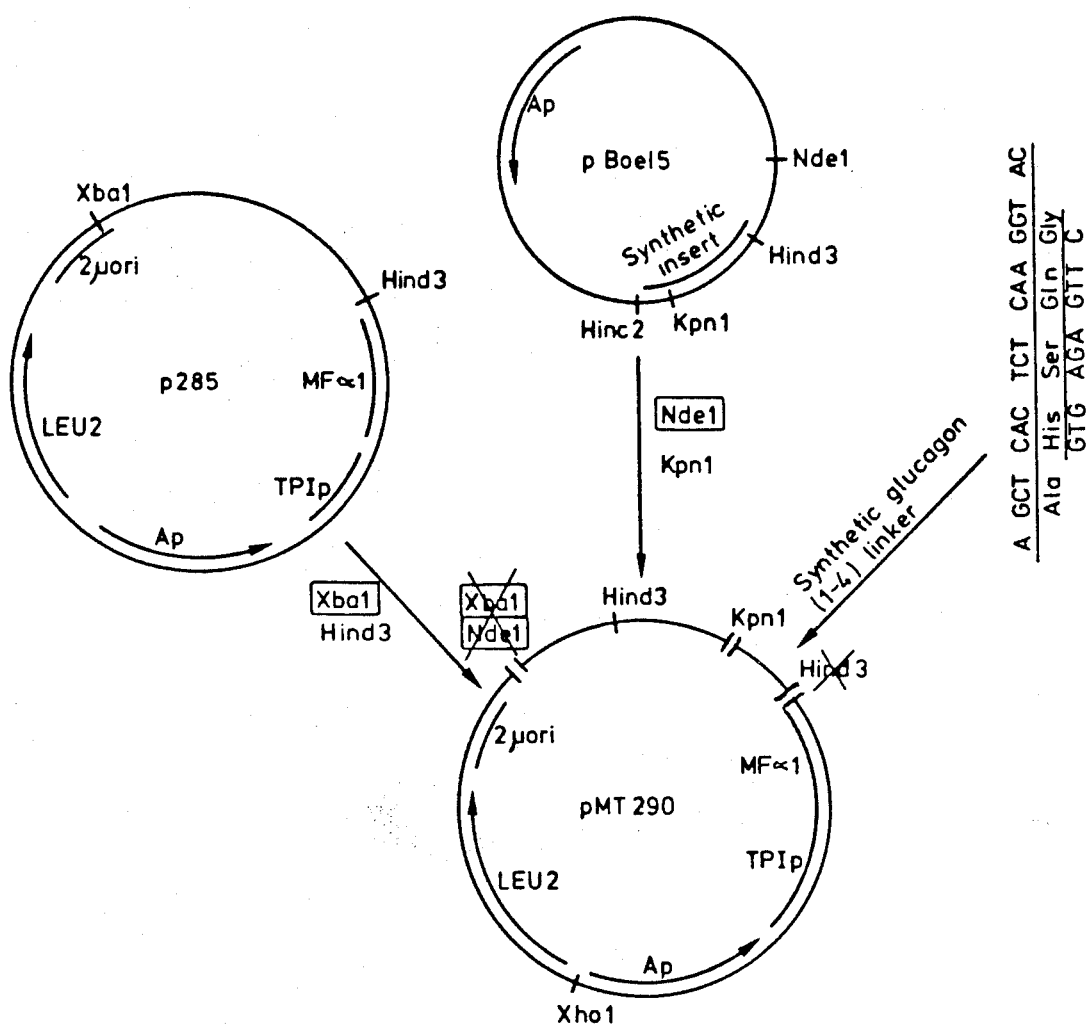
FIG. 1 illustrates the construction of plasmid pMT290.

From the above amino acid sequence (I) a synthetic gene sequence encoding glucagon(1-29) has been constructed from a number of oligonucleotides by use of amino acid codons preferably used for high expression of proteins in yeast (Bennetzen J. L. et al., (1982), The Journal of Biological Chemistry, 257, 3026-3031). Furthermore, restriction enzyme recognition sites were incorporated at appropriate sites in the molecule to enable the gene to be specifically dissected to aid characterisation and mutagenesis. An attempt was made to try to avoid secondary structures which would possibly counteract ligating and filling in reactions.

Synthetic genes coding for fragments or derivatives of glucagon can be constructed from the glucagon(1-29) gene. A synthetic gene coding for glucagon(1-21) was constructed by substitution of a synthetic DNA fragment corresponding to glucagon(16-21) for restriction fragment corresponding to glucagon(16-29) in the glucagon (1-29) gene. Preparing synthetic genes encoding other glucagon fragments or derivatives from the synthetic glucagon(1-29) gene or preparing a synthetic gene for such fragments or derivatives by oligonucleotide synthesizing of the whole gene for such products will be apparent to those skilled in the art.

The gene for glucagon(1-29) may also be derived from a cDNA glucagon clone. Bovine pancreatic preproglucagon cDNA has been isolated and sequenced (L. C. Lopez et al., (1983), Proc. Natl. Acad. Sci. USA, 80, 5485-5489). The preproglucagon cDNA encodes a signal or pre-peptide, an $NH_2$-terminal peptide, glucagon and two carboxy-terminal glucagon-like peptides (GLP-1 and GLP-2). For the purpose of the present invention the glucagon sequence may be dissected from the synthesized cDNA and provided with a stop codon after the codon for Thr(29) by site specific mutagenesis.

The gene for the desired product may be fused to a DNA-sequence encoding an additional protein having the function of protecting the expressed protein against, e.g. in vivo degradations by endogenous enzymes or of providing the information necessary to transport the expressed protein into the periplasmic space and finally across the cell wall into the culture medium.

If the gene is expressed as a fused product, means for cleaving the glucagon portion from such fusion product should be provided. For such purposes codons coding for an amino acid sequence containing a selective cleavage site are inserted between the DNA-sequence encoding the additional protein and the gene for the desired product. The additional protein may be split off during the secretion of the desired protein by means of the transformed microoganism itself. If for instance codons coding for two basic amino acids (e.g. Lys-Lys, Arg-Arg, Lys-Arg or Arg-Lys) are inserted adjacent to the N-terminal of glucagon the peptide bond between these basic amino acids and glucagon may be cleaved by yeast during secretion.

The desired protein may also be secreted with an additional protein sequence linked to the N-terminal of the desired protein provided that the additional protein contains a selective cleavage site adjacent to the N-terminal of the desired protein for later splitting of the superfluous amino acid sequence either by enzymatic or chemical means.

For secretion purposes the additional DNA-sequence may code for a signal peptide. The additional DNA sequence may further code for a leader peptide sequence. The signal and leader peptides are cleaved off by the transformant microorganism during the secretion of the expressed protein product from the cells ensuring a more simple isolation procedure of the desired product. A well suited leader peptide system for yeast is the yeast MFαl leader sequence or a part thereof (Kurjan, J. and Herskowitz, I., Cell 30 (1982) 933-943). However, any signal- or leader-sequence which provides for secretion in yeast may be employed and the present invention is not contemplated to be restricted to a specific secretion system.

For expression purposes a promoter sequence is positioned upstream to the DNA-sequence for the desired protein product. Preferably a promoter from a gene indigenous to the yeast host organism is used, e.g. the promoter of the TPI-(triose phosphate isomerase) gene. The DNA-sequence for the desired product will be followed by a transcription terminator sequence, preferably a terminator sequence from a gene indigenous to the host yeast organism, e.g. the terminator of the TPI-gene or the MFαl-gene.

The DNA-sequence encoding the desired protein product fused to appropriate promoter, leader and terminator sequences is inserted in an expression vehicle for expression of the desired protein product in yeast.

The expression vehicle may be a plasmid capable of replication in yeast or capable of integration into the yeast chromosome. The plasmid may preferably be stabilized against plasmid loss of the host microorganism by incorporation of a gene essential for the viability or normal growth of the host cells, e.g. a gene coding for cell division, cell wall biosynthesis, protein synthesis etc.

DETAILED DESCRIPTION

The synthetic gene for glucagon(1-29) was constructed from a number of oligonucleotides by ligation followed by enzymatic filling in of a partly double stranded structure.

The oligonucleotides were synthesized on an automatic DNA synthesizer using phosphoramidite chemistry on a silica support (S. L. Beaucage and M. H. Caruthers (1981) Tetrahydron Letters 22, 1859-1869) or by semiautomatical column synthesis using the phosphotriester approach with di- and trinucleotide blocks and a polystyrene support (H. Ito, Y. Ike, S. Ikata, and K. Itakura (1982) Nucleic Acids Res. 10, 1755-1769). The synthesis of oligonucleotides from smaller units by successive coupling reactions is well known in the art. A synthetic gene encoding glucagon(1-29) was synthesized as follows:

A 33-mer (I):

GAGCACTCTCAGGGTACCTTCACTTCT-GACTA  (I)

was ligated to a 33 mer (II)

TCTAAATACTTGGACTCTAGAAGAGC-CAAGAC  (II)

by means of a 13 mer (III):

ATTTAGAGTAGTC  (III)

resulting in a 66-mer (I-II):

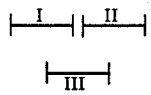

Furthermore, a 73-mer was synthesized by ligation of the 13-mer (III), a 16-mer (V):

CTTCTAGAGTCCAAGT  (V)

and a 44-mer (IV):

CCGAAGCTTAGGTGTTCATCAACCATT-
GGACGAAGTCTTGGGCT  (IV)

in the presence of the 33-mer (II)

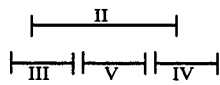

resulting in a 73-mer (III-V-IV).

The 66-mer (I-II) and the 73-mer (III-V-IV) the 3'-ends of which are complementary over 39 bases were annealed and the 3'-ends were prolongated enzymatically resulting in a 100 base pair double stranded DNA molecule shown in the following with incorporated restriction sites (capital letters: chemical synthesis, small letters: enzymatical prolongation):

```
|―――――――――――――― I ――――――――――――――|―――――――――――― II ―――――――――――|
 His—Ser—Gln—Gly—Thr—Phe—Thr—Ser—Asp—Tyr—Ser—Lys—Tyr—Leu—Asp—Ser—Arg—Arg
  1    2    3    4    5    6    7    8    9   10   11   12   13   14   15   16   17   18
 HgiAI     DdeI    KpnI                               Hinfl XbaI MboII GAG CAC TCT GAG GGT ACC TTC ACT TCT GAC TAC TCT AAA TAC TTG GAC TCT AGA AGA
ctc gtg aga gtc cca tgg aag tga aga CTG ATG AGA TTT ATG AAC CTA AGA TCT TCT
                                  |―――――――― III ――――――――|―――― V ――――|―
```

```
                |―――――――――――――――――|
 Ala—Gln—Asp—Phe—Val—Gln—Trp—Leu—Met—Asn—Thr—End
  19   20   21   22   23   24   25   26   27   28   29
 BanII    TthIII                           DdeI  Hind3

GCC CAA GAC ttc gtc caa tgg ttg atg aac acc taa gcttcgg
CGG GTT CTG AAG CAG GTT ACC AAC TAC TTG TGG ATT CGAAGCC
                       |―――――――――――――――――――――――――――――|
                                     IV
```

The Kpn1-Hind3 fragment of the synthetic gene was inserted in a plasmid (pLaC48 cut with Kpn1 and Hind3) by means of T4 ligase. The ligation mixture was used to transform competent *E. coli* cells. After retransformation a transformant (pKFN4) harbouring the correct sequence for glucagon(4-29) was identified.

The synthetic gene encoding glucagon(1-29) was then constructed by insertion of the glucagon(4-29)' gene in a yeast plasmid harbouring a synthetic glucagon(1-3) sequence. The ligation occurs in the Kpn1-site.

A synthetic gene encoding glucagon(1-21) was constructed from the glucagon(1-29) gene by substitution of a synthetic Xba1-Hind3 fragment corresponding to glucagon(16-21) for the Xba1-Hind3 fragment corresponding to glucagon(16-29):

```
        (S)er Arg Arg Ala Gln Asp End
         16   17  18  19  20  21  22
  XbaI                              Hind3
5' C T A G A A G A G C C C A A G A C T A
3'         T T C T C G G G T T C T G A T T C G G
```

PLASMID CONSTRUCTIONS

A synthetic oligonucleotide encoding the first four amino acids of glucagon and ending in a Kpn1 site was placed in a yeast vector after the MFα1 leader sequence (J. Kurjan and I. Herskowitz., Structure of a Yeast Pheromone Gene MFα: A Putative α-Factor Precursor Contains four Tandem Copies of Mature α-Factor. Cell 30 (1982) 933–943). The original Hind 3 site at the end of the α-factor leader was destroyed by the coupling.

The coupling is illustrated below:

```
| α-factor         | glucagon 1-4      |
  Glu  Ala  His  Ser  Gln  Gly  Thr
  "Hind3"                        Kpnl

A G C T C A C T C T C A A G G T A C
          G T G A G A G T T C
```

The resulting plasmid pMT290 had the promotor proximal part of the glucagon gene placed immediately after the Lys-Arg-Glu-Ala-Glu-Ala of the MFα1 leader and under TPI promoter (TPI*p*) control. This plasmid is suited for insertion of the sequence for glucagon(4-29) from plasmid pKFN4. The plasmid does not, however contain any yeast signal for termination of transcription. Such termination sites have been reported to increase the yield of a cloned protein by as much as ten fold (J. Mellor et al. Gene 24 (1983) 1–14). Therefore in the yeast expression vector pMT544 the α-factor transcription terminator (MFα1$_T$) sequence from pMT409 was placed after the glucagon insert.

Plasmid pMT544 containing the insert coding for TPI*p*-MFα1 leader-glucagon(1-29)-MFα1$_T$ did still contain the sequence coding for an N-terminal Glu-Ala-Glu-Ala extension which in our construction is only removed by the yeast in about one-third of the molecules. The DNA sequence encoding the C-terminal Glu-Ala-Glu-Ala of the MFα1 leader was removed from pMT544 by in vitro deletion mutagenesis. The resulting yeast expression plasmid pKFN6 contained the insert coding for TPI$_P$-MFα1 leader(minus Glu-Ala-Glu-Ala)-glucagon-(1-29)-MFα1$_T$.

In a preferred construction this expression unit was transferred to a stable, high copy number yeast plasmid CPOT (ATCC No. 39685), which can be selected merely by the presence of glucose in the growth medium. The resulting yeast expression plasmid for glucagon(1-29) was numbered pMT612.

A plasmid containing the insert coding for TPI$_P$-MFα1 leader(minus Glu-Ala-Glu-Ala)-glucagon(1-21)-MFα1$_T$ was constructed from pKFN6 by substitution of a synthetic Xba1-Hind3 fragment encoding glucagon(16-21) for the Xba1-Hind3 fragment encoding glucagon (16-21).

In a preferred construction the above mentioned expression unit was transferred to yeast plasmid CPOT (ATCC No. 39685). The resulting yeast expression plasmid for glucagon(1-21) was numbered pKFN23.

TRANSFORMATION

Plasmid pMT612 was transformed into S. cerevisiae strains carrying deletions in the triose phosphate isomerase (TPI) gene by selecting for growth on glucose. Such strains are normally unable to grow on glucose as the sole carbon source and grow very slowly on galactose lactate medium. This defect is due to a mutation in the TPI gene, obtained by deletion and replacement of a major part of this gene with the S. cerevisiae LEU 2 gene. Because of the growth deficiencies there is a strong selection for a plasmid which contains a gene coding for TPI. pMT612 contains the Schizo. pombe TPI gene.

Plasmid pMT544 was transformed into a S. cerevisiae LEU 2 mutant by selection for leucin prototrophy (A. Hinnen, J. B. Hichs and G. R. Fink, "Transformation of Yeast", Proc. Nat. Aca. Scc. 75 (1978) 1929).

Plasmid pKFN23 was transformed into a S. cerevisiae strain carrying deletions in the TPI gene by selecting for growth on glucose. A transferred strain KFN31 was selected for further use.

A transformed strain MT615 harbouring the plasmid pMT612 was deposited by the applicant with Deutsche Sammlung von Mikroorganismen (DSM), Griesebachstrasse 8, D-3400 Göttingen, on Jan. 10, 1985 and accorded the reference number DSM 3184.

Strain KFN31 was deposited by the applicant with DSM on Dec. 13, 1985 and accorded the reference number DSM 3608. DSM being an international depository authorized under the Budapest Treaty of 1977, affords permanence of the above deposits and accessibility thereto by the public in accordance with Rules 9 and 11, respectively, of the above treaty.

EXPERIMENTAL PART

EXAMPLE 1

Oligodeoxyribonucleotide synthesis

Protected deoxyribonucleoside 3'-p-chlorophenylphosphates as well as protected di- and trinucleotide 3'-p-chlorophenylphosphates were prepared as described (G. R. Gough, K. J. Collier, H. L. Weith, and P. T. Gilham (1979) Nucleic Acids Research 7, 1955-1964).

Pyridine was rendered anhydrous by reflux over and then distillation from calcium hydride.

The support for oligonucleotide synthesis by the phosphotriester approach was fully protected deoxyribonucleosides bound via a 3'-O-succinyl group to aminomethylated 1% crosslinked polystyrene beads (Bachem).

The synthesis of 33-mer (I) was started with 3 μmole of DMTr-dA$^{Bz}$-polymer which was packed in a column (Omnifit, 6.5 mm i.d.). Solvents and reagents were delivered to the column by means of an HPLC pump (Kontron LC Pump 410) and a control module (Kontron Programmer Model 200) via a pneumatically activated six port rotary valve (Rheodyne model 5011). The first cycle consisted of removal of the dimethoxytrityl groups with 10% trichloroacetic acid in chloroform followed by washing with chloroform and pyridine. The coupling reaction was performed by manual injection of 0.1M dimethoxytrityl thymidine 3'-O-p-chlorophenylphosphate, 0.3M 1-mesitylenesulfonyl-3-nitro-1,2,4-triazole and 1M N-methylimidazole in anhydrous pyridine (B. S. Sproat and W. Banwarth (1983) Tetrahedron Letters 24, 5771-5774). After coupling at room temperature for 30 minutes the polymer was washed with pyridine and chloroform. The cycle time was 85 minutes. In a similar way protected di- and trinucleotide 3'-O-p-chlorophenylphosphates were coupled to the growing oligonucleotide on the support. The fully protected 33-mer was partly deprotected and cleaved from the support by treatment with 0.5M tetramethylguanidinium pyridine-2-aldoximate in pyridine-water (4:1) at 37° C. for 24 hours. (C. B. Reese, R. C. Titmas, and L. Yau (1978) Tetrahedron Letters, 2727-2730). The base protecting groups were removed by treatment with conc. ammonia at 55° C. for 24 hours. Finally the dimethoxytrityl groups were removed by treatment with 80% aqueous acetic acid at room temperature for 30 minutes. The 33-mer (I) was purified by HPLC on a C18 column as described (H. J. Fritz, R. Belagaje, E. Brown, R. H. Fritz, R. A. Jones, R. G. Lees, and H. G. Khorana (1978) Biochemistry 17, 1257-1267).

In a similar way were synthesized 13-mer (III), 16-mer (V), 44-mer (IV), and the two oligonucleotides (10-mer and 18-mer) used as a synthetic glucagon (1-4) linker for the fusion of the α-factor leader sequence and the glucagon (1-29) gene. 33-mer II, the two 19-mers used in the construction of the gene for glucagon (1-21) and the 26-mer mutagenic deletion primer were synthesized on an automatic DNA synthesizer (Applied Biosystems Model 380A) using phosphoramidite chemistry and commercially available reagents.

EXAMPLE 2

Synthesis of a gene encoding glucagon (4-29)

Oligonucleotides were labelled at the 5'-end as described (K. Norris, F. Norris, L. Christiansen, and N. Fiil (1983) Nucleic Acids Research 11, 5103–5112).

A mixture of 10 pmole each of I and 5'-$^{32}$P-labelled II and 20 pmole of III in 10 μl water was heated at 60° C. for 5 minutes and then chilled in ice. 10 μl of 132 mM Tris-HCl(pH 7.4), 20 mM MgCl$_2$, 2 mM ATP, 20 mM DTT, 100 μg/ml gelatine and 0.5 μl T4 ligase (200 units) was added. The ligation reaction was carried out at 16° C. for 2.5 hours where about ⅔ were ligated. The resulting 66-mer (I-II) was purified by denaturing PAGE and buffer elution.

Similarly 20 pmole of 5'-$^{32}$P-labelled V was ligated with 20 pmole of 5'-$^{32}$P-labelled (III) and 20 pmole of IV in the presence of 25 pmole of II at 16° C. for 2.5 hours. The resulting 73-mer (III-V-IV) was purified by denaturating PAGE and buffer elution.

2 pmole each of (I-II) and (III-V-IV) in 9 µl 50 mM Tris-HCl (pH 7.8), 5 mM MgCl$_2$, 10 mM DTT and 50 µg/ml gelatine were heated for 3 minutes at 80° C. and then cooled over 30 minutes to 45° C. After annealing for 15 minutes at 45° C. the reaction mixture was cooled to 16° C. and 1 µl dNTP-mix (dATP, dCTP, dGTP, dTTP, 5 mM each) and 1 µl DNA polymerase I, Klenow fragment (3.5 units) were added. The filling in reaction was allowed to proceed for 60 minutes at 16° C., and then the DNA was isolated by phenol extraction and ethanol precipitation. The DNA was digested with Kpn1 and Hind3 and ligated to the large Kpn1-Hind3 fragment from plasmid pLaC48 (a derivative of pBR322 containing unique Kpn1 and Hind3 sites).

The ligation mixture was transformed into competent E. coli cells selecting for ampicillin resistance. By restriction enzyme analysis (Xba1, Kpn1 and Hind3) and DNA sequencing (A. Maxam and W. Gilbert (1980) Methods Enzymol. 65, 499–560) a colony harbouring a plasmid pKFN4 containing the synthetic glucagon (4-29) gene was identified.

EXAMPLE 3

Construction of yeast plasmids for expression of glucagon (1-29)

Plasmid p285 was cut with restriction enzyme Xba1 and then blunt-ended by treatment with Klenow polymerase and deoxyribonucleotidetriphosphates. After phenol extraction, ethanol precipitation and resuspension the DNA was cut by Hind 3 and a 10.5 kb fragment was isolated. This fragment contained the TPI promoter (T. Alber and G. Kawasaki, J. Mol. Applied. Genet., 1 (1982), 419-434) and the MFα1 leader sequence. The construction of p285 is described in U.S. patent application Ser. No. 547,748 of Nov. 1, 1983. p285 contains the insert TPI$_P$-MFα1 leader B-C-A-TPI$_T$ and was deposited in yeast strain Z 33 (ATCC No. 20681). Plasmid pBoe15 (a derivative of pUC8 with a synthetic Hinc 2, Hind 3 insert containing a Kpn1 site) was cut with restriction enzyme Nde1, blunt-ended by means of Klenow polymerase as above and cut with Kpn1 and finally a 0.3 kb fragment was isolated. These two fragments were ligated by means of the synthetic glucagon(1-4) linker prepared as described above connecting the Kpn1 site of the pUC8 insert to the Hind 3 site at position 263 of the MFα1 leader sequence. In order to avoid insertion of multiple copies, the linker was not phosphorylated prior to ligation. The original Hind 3 site at the end of the MFα1 leader was not reformed by the linker. The ligation mixture was transformed into E. Coli selecting for ampicillin resistance.

A plasmid, pMT290 (FIG. 1), containing the desired restriction pattern was obtained.

Figure 2:
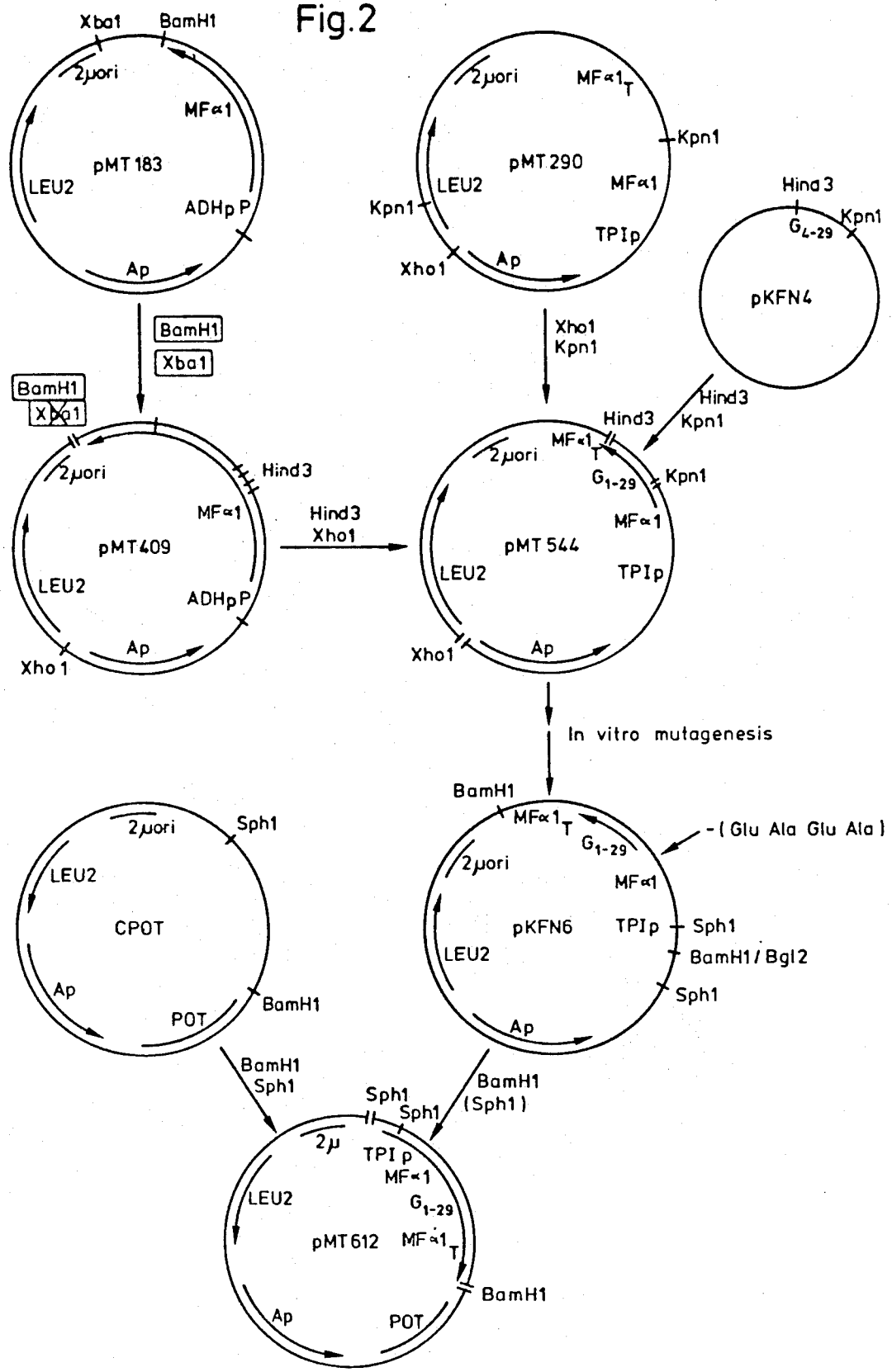
FIG. 2 illustrates the construction of plasmids pMT544, pKFN6 and pMT612.
Figure 3:
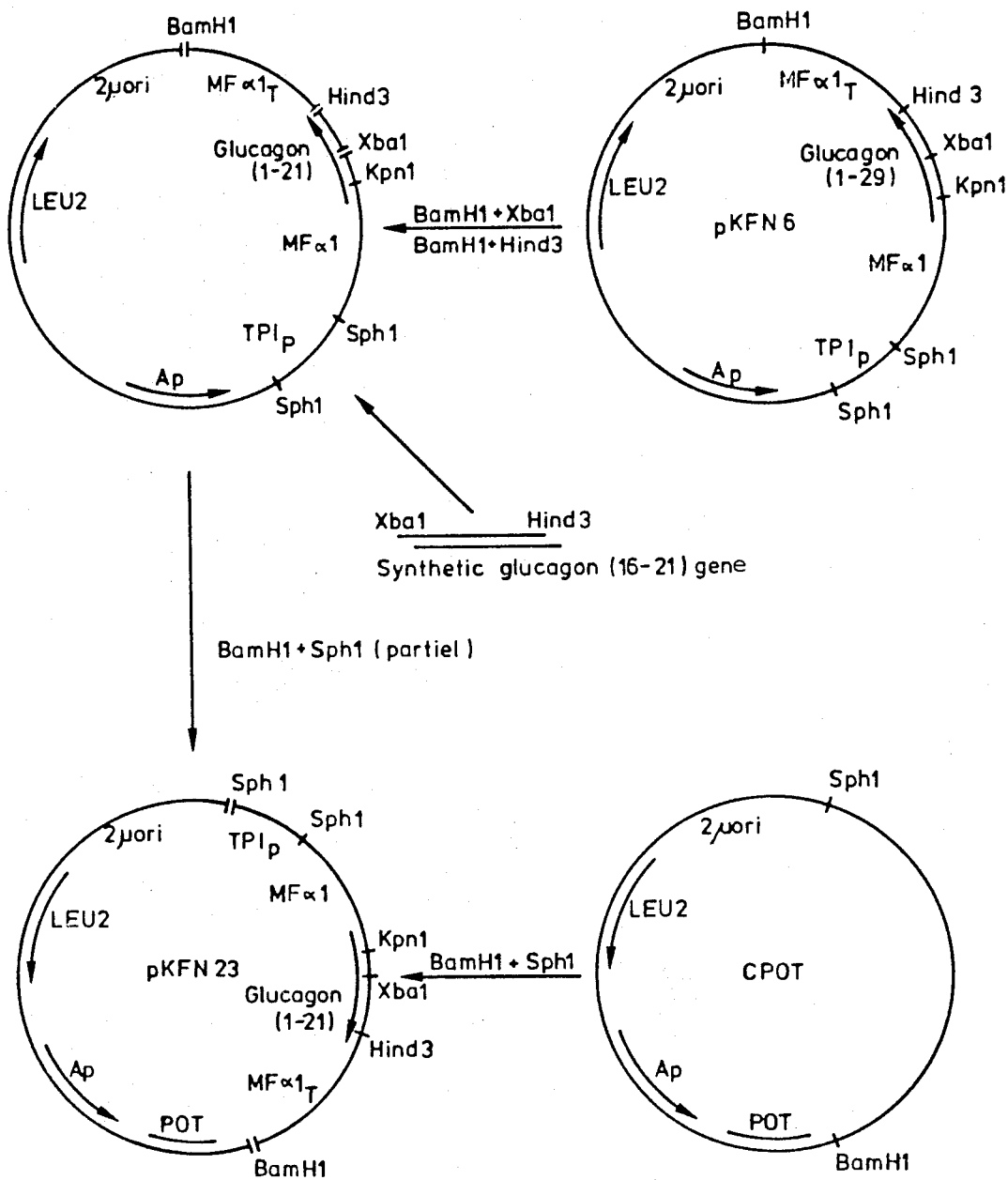
FIG. 3 illustrates the construction of plasmid pKFN23.
Figure 4:
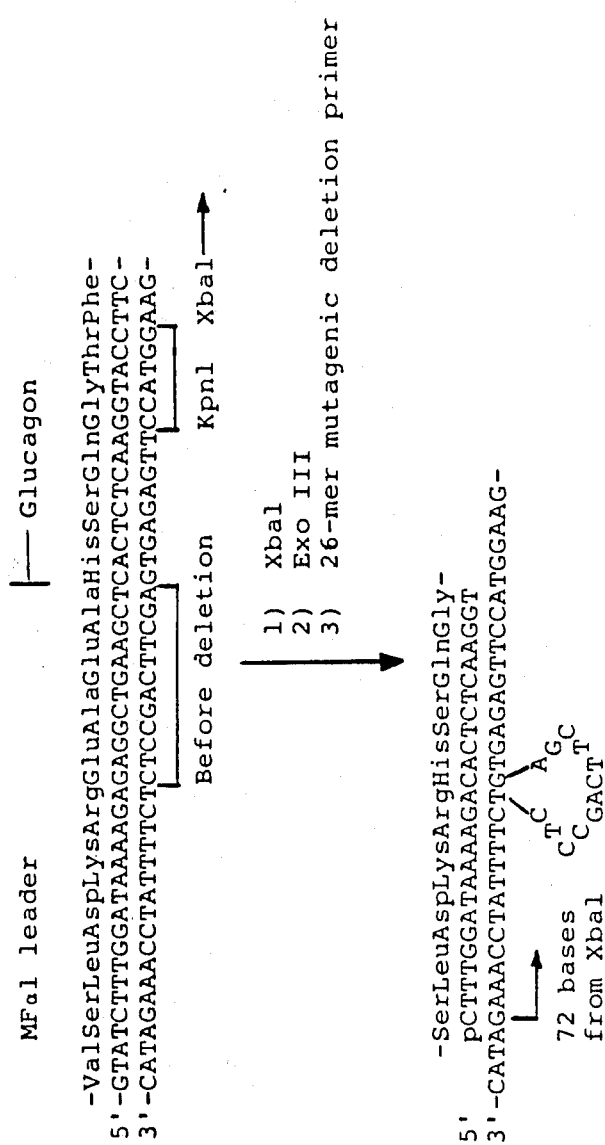
FIGS. 4 and 5 illustrate in vitro mutagenesis of a certain sequence from plasmid pMT544.

To obtain an expression plasmid containing the entire gene coding for glucagon(1-29) and also containing a transcription termination sequence following the gene, a 6.5 kb Xho1-Kpn1 fragment from pMT290 was ligated to a 5.1 kb Hind3-Xho1 fragment from pMT409 (pMT183 with a 0.7 kb Xba1-BamH1 deletion) and to the synthetic Kpn1-Hind3 fragment encoding glucagon(4-29) from pKFN4. Plasmid pMT183 is a derivative of YEP 13 containing a 2.1 kb Sph1-BamH3 insert. The insert codes for expression of the MFα1 gene of S. cerevisiae under the control of the alcohol dehydrogenase promoter from Schizzosaccharomyces pombe. The insert, in its BamH3 promixal part, also contains the sequences from the MFα1 gene which specify transcription termination. The ligation mixture was transformed into E. Coli selecting for ampicillin resistance. One of the resulting plasmids, pMT544 (FIG. 2) which shows the expected restriction pattern codes for the expression of glucagon(1-29) but still contains the sequence coding for an N-terminal Glu-Ala-Glu-Ala extension. The sequence coding for Glu-Ala-Glu-Ala was removed from pMT544 by in vitro mutagenesis to give pKFN6. pMT544 was linearized by cutting in the unique Xba1 site in the glucagon gene. 5'-mononucleotides were removed from the 3'-ends of the obtained double stranded DNA by means of Exo III nuclease treatment. The Exo III nuclease treatment was performed at 23° C. under conditions where about 250 nucleotides were removed from each 3'-end of the linearized plasmid (L. Guo and R. WU. (1983), Methods in Enzymology 100, 60–96). A kinased 26-mer mutagenic deletion primer d(CTTTGGATAAAAGACACTCT-CAAGGT) was annealed to the mutation site (FIG. 4). A double stranded circular DNA was made by filling in with Klenow polymerase and ligation with T4 ligase. The original Xba1 site in the glucagon gene was destroyed by the Klenow filling in and following ligation. After transformation of E. coli (MT172) mutants were identified by colony hybridization with the 5'-$^{32}$P-labelled 26 mer deletion mutagenesis primer. Plasmid from 8 mutants were analyzed by Kpn1+Pst1 digestion, whereby the intended deletion of 12 based was confirmed. 3 of the 8 mutants were "pure" mutants but plasmids from these were nevertheless retransformed in E. coli (MT172).

Figure 5:
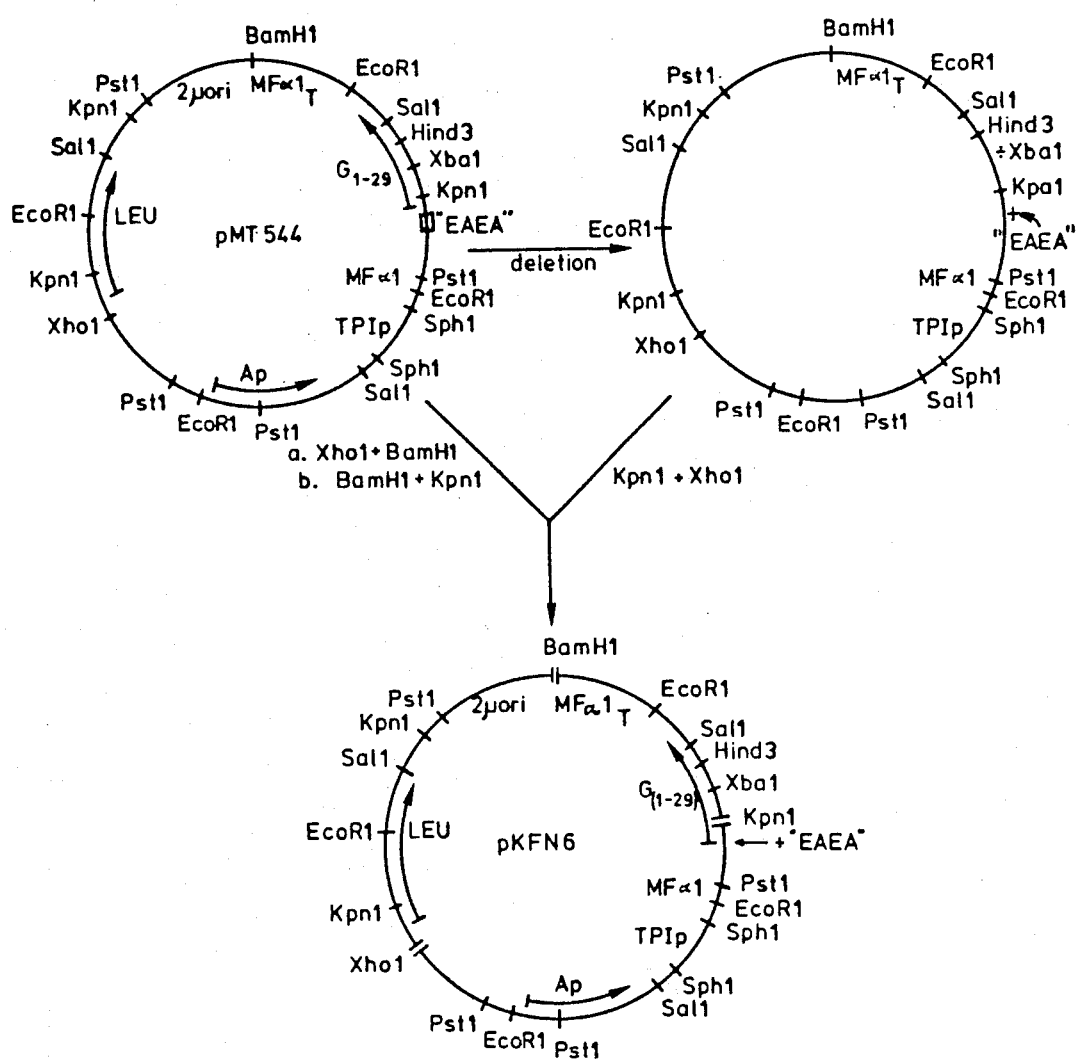

The destroyed Xba1 site in the glucagon gene was then reconstructed by ligation of a 4.4 kb BamH1-Xho1 and a 0.9 kb BamH1-Kpn1 fragment (containing the glucagon (4-29) gene) from pMT544 with a 6.6 kb Xho1-Kpn1 fragment from two plasmids with the 12 bp deletion (see FIG. 5).

The two ligation mixtures were used to transform (E. Coli (MT172) and plasmid isolated from the transformants were screened for the presence of a Xba1 site (Xba1+EcoR1 digestion). The deletion was confirmed by DNA sequencing (A. Maxam and W. Gilbert (1980) Methods in Enzymology 65, 499–560) of a Xba1-Sal1 fragment from 4 plasmids. One plasmid, pKFN6, was selected for further use.

A 2.1 kb BamH1-Sph1 (partial) fragment from pKFN6 containing the TPI$_P$-MFα1 leader(minus Glu Ala Glu Ala)-glucagon(1-29)-MFα1$_T$ was ligated to an approximately 11 kb BamH1-Sph1 fragment of plasmid CPOT containing the S. pombe TPI gene. The ligation mixture was transformed into E. Coli selecting for ampicillin resistance. The resulting plasmid was pMT612 (see FIG. 2).

EXAMPLE 4

Construction of yeast plasmids for expression of glucagon(1-21)

A 0,9 kb BamH1-Hind3 fragment and a 11 kb Xba1-BamH1 fragment, both from pKFN6, were ligated to a synthetic 19 bp Hind3-Xba1 fragment encoding glucagon(16-21) (see above). The ligation mixture was transformed into E. coli (MT 172) selecting for ampicillin resistance. Plasmid from 12 transformants were analyzed by BamH1+Xba1 digestion. A 2.1 kb BamH1-Sph1 (partial) fragment from one of the plasmids was then ligated to an approximately 11 kb BamH1-Sph1 fragment from plasmid CPOT containing the *S. pombe* TPI gene. The ligation mixture was transformed into *E. coli* (MT 172) selecting for ampicillin resistance.

By restriction enzyme analysis (BamH1+Xba1 and Hind3+Pst1) and DNA sequencing of a 0.7 kb $^{32}$P-labelled Sal1-Sph1 fragment a colony harbouring a plasmid pKFN23 containing the synthetic glucagon(1-21) gene was identified.

EXAMPLE 5

Expression of glucagon (1-29) in yeast strain MT556

*S. cerevisae* strain 362 (leu 2) was grown on YPD medium (Sherman et al., Methods in Yeast Genetics, Cold Spring Harbor Laboratory, 1981) to an O.D.$_{600}$ of 2.1. 100 ml of culture was harvested by centrifugation, washed with 10 ml of water, recentrifuged and resuspended in 10 ml of (1.2M sorbitol, 25 mM Na$_2$EDTA pH=8.0, 6.7 mg/ml dithiotreitol). The suspension was incubated at 30° C. for 15 minutes, centrifuged and the cells resuspended in 10 ml of (1.2M sorbitol, 10 mM Na$_2$EDTA, 0.1M sodium citrate pH=5.8, 2 mg Novozym ® 234). The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 nM Tris (Tris=Tris(-hydroxymethyl)-aminometan) pH=7.5) and resuspended in 2 ml of CAS. For transformation 0.1 ml of CAS-resuspended cells were mixed with approximately 1 μg of plasmid pMT544 and left at room temperature for 15 minutes. 1 ml of (20% polyethylenglycol 4000, 10mM CaCl$_2$, 10 mM Tris pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl$_2$, 14 μg/ml leucine) and incubated at 30° C. for 2 hours. The suspension was then centrifuged and the pellet resuspended in 0.5 ml of 1.2M sorbitol. 6 ml of top agar (the SC medium of Sherman et al., (Methods in Yeast Genetics, Cold Spring Harbor Laboratory, 1981) with leucine omitted and containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant MT556 (=MT 362/pMT544) was chosen for further characterization.

Strain MT566 was grown in a synthetic complete medium SC (Sherman et al. Methods in Yeast Genetics, Cold Spring Harbor Laboratory 1981) with leucine omitted. A 1 liter culture in 2 liter baffled flasks was shaken at 30° C. until an O. D.$_{600}$ nm of 7 to 10. The culture was then centrifuged and the supernatant removed for further analysis.

Glucagon like immunoreactivity (GLI) was measured in the supernatant from MT556 by radioimmunoassay with antiglucagon serum K-6248 (Heding L. G., (1983) Handbook of Experimental Pharmacology, Glucagon I: P. J. Lefebvre Ed. Springer Verlag pp. 189-202). This antibody recognizes the sequence in the middle of the glucagon molecule.

The expression levels of immunoactive glucagon (1-29) in the transformed yeast cells was 177 nmol/liter supernatant.

GLI-peptides were recovered from MT556 supernatant. To 800 ml of the supernatant was added $^{125}$I-glucagon tracer and 96% EtOH to obtain an alcohol concentration of 5% (v/v). The supernatant was concentrated on a Sep-Pak ® column (Waters) and ⅔ of the concentrate corresponding to 533 ml supernatant was purified on an antiglucagon immunoabsorbant column.

The eluate from the antiglucagon column was fractionated on a HPLC on a 10μ waters μBondopak C-18 column (3.9×300 mm). The A and B buffers were 0.1% TFA in H$_2$O and 0.07% TFA in MeCN, respectively. The column was equilibrated with 25% B (flow: 1.5 ml/minute) and the peptides were eluted with a linear gradient of MeCN (1%/minute) and detected at 276 nm.

The peak corresponding to GLI eluates in the same area as pancreatic glucagon 1-29 standard. This fraction was concentrated, redissolved and subjected to an amino acid sequence analysis. The sequence analysis of the isolated peptides was performed with a Gas Phase Sequencer (Moody, A. J., Thim, L., Valverde, I. FEBS Lett., 172 (1984), 142-148).

The following results were obtained:

| | Purificaton of GLI—peptides from MT556 | | |
|---|---|---|---|
| | Vol | GLI (antibody K-6248) | Yield |
| Step | ml | nmol | % |
| Supernatant | 800 | 142 | 100 |
| Sep-Pak concentrate | 2 | 111 | 78 |
| Antiglucagon column | 0.2 | 29 | 20 |
| HPLC | 2.0 | 11 | 8 |

From the sequencing results it could be concluded that the expression products consisted of three peptides:

| | |
|---|---|
| Glu—Ala—Glu—Ala—Glucagon(1-29) | 33% |
| Glu—Ala—Glucagon(1-29) and | 33% |
| glucagon(1-29) | 33% |

The three peptides were present in the relative amounts as indicated.

It could furthermore be concluded that the Arg-Arg-sequence was intact in all three peptides.

EXAMPLE 6

Expression of glucagon (1-29) in yeast strain MT 615

*S. cerevisiae* strain MT501 (E2-7B×E11-3C (a/α, Δtpi/Δtpi, pep4-3/pep4-3)) was transformed with pMT612 as described in Example 4 with the following modifications: (1) prior to transformation strain MT501 was grown on YPGaL (1% Bacto yeast extract, 2% Bacto peptone, 2% galactose, 1% lactate) to an O.D.$_{600}$ of 0.6 (2) the SOS solution contained YPGaL instead of YPD. One transformant MT615 (=MT501/pMT612) was chosen for further characterization. Strain MT615 was grown as described for MT556 but on an YPD medium (Sherman et al., Methods in Yeast Genetics, Cold Spring Habor Laboratory, 1981) and to an O.D.$_{600}$ of 15.

Glucagon was isolated from MT 615 supernatant. Two isolations have been carried out. In the first, peptides from the supernatant were bound to a column of Merck C18, eluted with 60% ethanol and then fractionated on a Waters HPLC SP ionexchanger. This approach was only partially successful since the $^{125}$I-glucagon used as a tracer was quantitatively precipitated during preparation of the C18 eluate for separation on SP. In the second, the peptides in MT 615 supernatant were bound to SP Sephadex, eluted and fractionated by reverse phase HPLC. Recovery of GLI was measured by RIA (Heding L. G. (1971) Radiological determination of pancreatic and gut glucagon in plasma, Diabetologia 7, 10–19) using antiglucagon serum K6248 and K5563 (which recognizes the C terminal portion of glucagon), (Heding L. G., (1983) Handbook of Experimental Pharmacology, Glucagon I: P. J. Lefebvre, Ed. Springer Verlag pp. 189-202).

Isolation 1

$^{125}$I-porcine glucagon was added to 900 ml of MT 615, batch 1, and 800 ml fractionated as follows. The sample was adjusted to 5% ethanol and applied to a 4.8×1.5 cm column of Merck Lichroprep C18 (25–40μ) at about 200 ml/hr. After washing the column with 50 ml of 5% ethanol in 25 mmol/l ammonium formate, pH 3.5 and 15% ethanol in the same buffer, the retained peptides were eluted with 60% ethanol in ammonium formate.

On diluting the crude peptides in water (to reduce both the ionic strength and % organic solvent), a copious precipitate formed which contained the bulk of the $^{125}$I-glucagon. This precluded the planned use of a SP ionexchanger at pH 3-5. The precipitate was dissolved at pH 9.0, and reprecipitated at pH 4.0. The sample was dissolved in 2.5 mmol/l ammonium formate, pH 7.5, in 20% acetonitrile for fractionation on a Waters DEAE ionexchanger. When the sample was applied the $^{125}$I-glucagon failed to bind. The breakthrough from the DEAE column was, therefore, concentrated in vacuo and the peptides fractionated by reverse phase HPLC on a 250×4.6 mm column of Nucleosil 5μ C18.

Isolation 2

Two grams of SP Sephadex C25 (other ionexchangers with suitable characteristics can be used) were added to 200 ml MT 615, batch 2, (pH adjusted to 4.3) and the suspension stirred for 20 minutes at room temperature. The SP Sephadex was filtered off in a 2.5 cm diameter glass chromatography column, washed with 50 ml 25 mmol/l ammonium formate, pH 3.5 and the bound peptides eluted with 500 mmol/l ammonium formate pH 8.4. Glucagon was isolated from this eluate by reverse phase HPLC on a 250×4.6 mm column of Nucleosil C18.

The distribution of glucagon-like immunoreactivity (GLI) during the fractionation was measured by RIA using antibodies which recognize glucagon 11-15 and the C-terminal portion of glucagon (K 6248 and K 5563, respectively).

The amount of HPLC "glucagon" in the fractions was estimated by HPLC. The procedure used was to analyze a sample without added glucagon and then identify "glucagon" by adding an internal standard of glucagon. The uv of the "glucagon" peak, was then used to calculate the amount of HPLC "glucagon" in the sample. The base-line for the estimation of peak-height was the u.v. trace adjacent to the "glucagon" peak. It was assumed that 1 mg (290 nmol) of glucagon/ml has an absorbtion of 2.0 cm$^{-1}$ at 276 nm.

RESULTS

The contents of HPLC "glucagon" and GLI in MT 615, batch 1 and 2, are given in Table 1.

Figure 6:
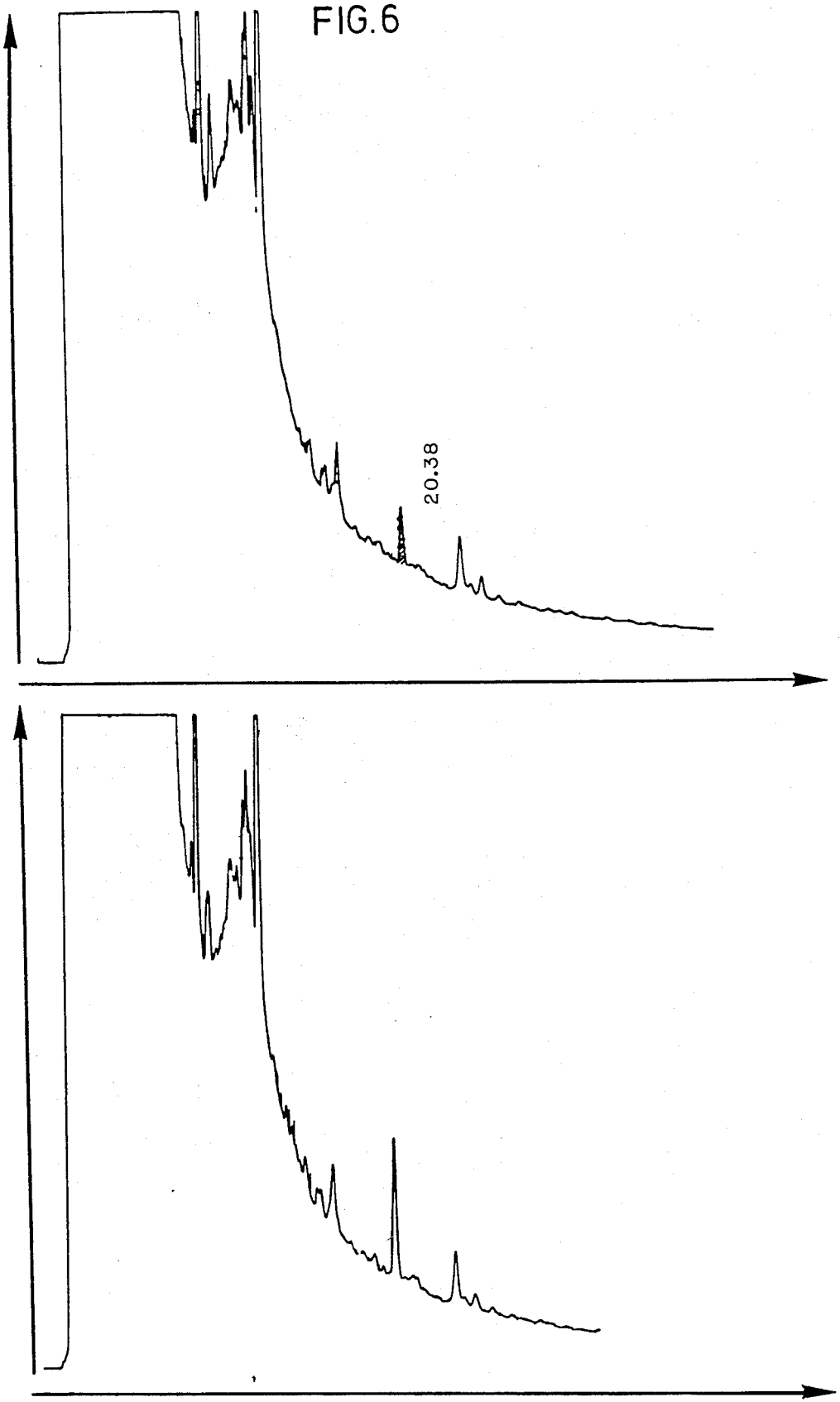
FIG. 6 shows an analytical HPLC profile of a yeast supernatant before and after addition of pure authentic glucagon.

An analytical HPLC profile of untreated MT 615 supernatant (Batch 1) alone (upper panel) and after addition of 3 μg glucagon (lower panel) is shown in FIG. 6. The column was a Macherey-Nagel Nucleosil 5 micron C18,250×4.6 mm equilibrated with 100 mmol/l ammonium formate, pH 3.5, in 25% acetonitrile at 1.0 ml/min. After two minutes the sample was eluted with a gradient of acetonitrile in ammonium formate (25% to 30% during 3 mins then 30% to 40% during 35 mins). The u.v. absorbance of the effluent was monitored at 280 nm, full scale 0.08 A units. The HPLC "glucagon" is hatched in the upper panel. It can be seen that a peptide peak ($R_t$ 20.38) was increased by the addition of glucagon and it was assumed that this material was HPLC "glucagon".

The preparative fractionation of the concentrated DEAE breakthrough is shown in FIG. 7. The HPLC separation was carried out as for FIG. 6 except that the u.v. absobance was measured at 280 nm, full scale 1.28 A units. The upper panel shows the preparative HPLC separation of concentrated DEAE breakthrough and the lower panel shows the distribution of GLI in the fractions. The effluent from the column was reduced in vacuo, freeze dried and dissolved in 0.1% acetic acid in 60% ethanol for GLI assay. The "glucagon" $R_t$ 20.51 has been fully sequenced and shown to be glucagon.

The recoveries from MT 615, batch 1, of $^{125}$I-glucagon, HPLC "glucagon" and GLI during the fractionation are summarized in Table 2 and the recovery of HPLC "glucagon" from batch 2 is summarized in Table 3.

It is concluded that the yeast construction MT 615 produces glucagon in the range of 250–1000 nmol/l (as judged by HPLC).

TABLE 1

"GLUCAGON" IN 2 BATCHES OF MT 615

| Batch | HPLC Glucagon (nmol/l) | GLI (nmol/l) K6248 | K5563 |
|---|---|---|---|
| MT 615, batch 1 | 250 | 1516 | 557 |
| MT 615, batch 2 | 960 | 3708 | 2145 |

TABLE 2

RECOVERY OF "GLUCAGON" FROM MT 615, BATCH 1

| SAMPLE | $^{125}$I-GLUCAGON % | HPLC "GLUCAGON (nmol) | GLI (nmol)$^a$ K6248 | K5563 |
|---|---|---|---|---|
| Start (800 ml) | 100 | 197 | 1212 | 446 |
| Lichroprep 60% ethanol (30 ml) | 81 | 91 (46%) | 690 | 600 |
| DEAE Start (24 ml) | 72 | 48 (24%) | 421 | 448 |
| DEAE B$_T$(35 ml) | 47 | 67 (34%) | 287 | 404 |
| PREP HPLC Start (2 ml) | 35 | 31 (16%) | 200 | 200 |
| "GLUCAGON" (0.5 ml) | n.d. | 44 (22%) | 31 (3%) | 43 (10%) |

$^a$some dilution effect in most samples and values given are means of 2 or 3 dilutions.

TABLE 3

RECOVERY OF "GLUCAGON" FROM MT 615, BATCH 2

| SAMPLE | HPLC GLUCAGON (nmol) |
|---|---|
| Start (200 ml) | 192 |
| SP FILTRATE (215 ml) | 40 (21%)[a] |
| SP ELUATE (18 ml) | 117 (61%) |
| HPLC - C18 (1 ml) | 118 (61%) |

[a] "Glucagon" peak very small and difficult to quantify.

EXAMPLE 7

Expression of glucagon(1-21) in yeast strain KFN31

S. cerevisiae strain MT663 (2/α, tpi/tpi, pep4-3/pep4-3) was transformed with pKFN23 as described in Example 6. One transformant KFN31 (=MT663/pKFN23) was chosen for further characterization. Strain KFN31 was grown as described for MT613 (see example 6) to an O. D.$_{600}$ of 15.

Expression level

The amount of glucagon(1-21) in the yeast supernatant was determined by analytical HPLC in the following system:

Solvent A: 0.1% (v/v) trifluoroacetic acid (TFA) in $H_2O$
Solvent B: 0.07% (v/v) TFA in acetonitrile (MeCN)
Column: RP-C18 Nova-pak®, 5μ, 4.6×150 mm (Waters)
Flow: 1.5 ml/min.
Detection: UV-absorption at 280 nm
Elution procedure:
  0–2 min: isocratic elution at 10% B/90% A
  2–22 min: gradient elution from 10% B/90% A to 30% B/70% A corresponding to 1% MeCN/min.
Standard: Synthetic glucagon(1-21) (NOVO Industri A/S) In the above HPLC-system, glucagon(1-21) eluted with a retention time of 17.36 min. By injection of different amounts of yeast strain KFN31 supernatant the expression level of glucagon(1-21) was determined to: 0.88 μmol/l ("HPLC"-glucagon(1-21)).

Purification of glucagon(1-21)

A column (1×9 cm) of LiChroprep® RP-18 (Merck, art. 9303) was washed with 30 ml of 50 mM $NH_4HCO_3$ containing 60% (v/v) ethanol. The column was then equilibrated with 50 mM $NH_4HCO_3$ containing 5% (v/v) ethanol. 23.5 ml of 96% ethanol were added to 450 ml of supernatant and the mixture was pumped through the column overnight (flow 25 ml/h). The column was washed with 15 ml of 0.1M NaCl and then with 15 ml of $H_2O$ and peptide material was eluted with 50 mM $NH_4HCO_3$ containing 60% (v/v) ethanol. Fractions of 3 ml were collected. The peptide material eluted in fractions Nos. 6 and 7, and these fractions were pooled and concentrated to 1 ml by vacuum centrifugation (Savant vacuum centrifuge) in order to remove the ethanol. 1 ml of 25 mM HEPES buffer, pH=7.4, was added to the concentrate, which was applied to an anti-glucagon Sepharose column (1.5×2.5 cm), which, prior to the application, had been equilibrated with 10 ml of 25 mM HEPES buffer, pH=7.4. After the application the column was allowed to stand for 30 min. at room temperature, and was thereafter washed with 10 ml of 25 mM HEPES buffer, pH=7.4. The peptide material was eluted with 20% (v/v) acetic acid, and the pH of the eluate was adjusted to 7.0 with $NH_4OH$.

The eluate from the previous step was concentrated to 500 μl by vacuum rotation and glucagon(1-21) was further purified by reverse phase HPLC by means of the system described above. The sample was divided into five aliquots, each of a volume of 100 μl. Peptide material eluting as a peak corresponding to a retention time of 17.36 min. was collected. The peptide material was dried in a vacuum centrifuge and redissolved in 100 μl of 0.1% (v/v) of acetic acid. The overall yield of glucagon(1-21) was 85%. Characterization The purified glucagon (1-21) was characterized by amino acid analysis (Thim, L. and Moody, A. J., Biochim. Biophys. Acta 703 (1982) 134–141) and amino acid sequence analysis (Moody, A. J., Thim, L. and Valverde, I. FEBS Lett., 172 (1984), 142–148). The results are shown in tables 4 and 5, respectively.

TABLE 4

Amino acid analysis of glucagon(1-21) purified from yeast strain KFN-31.

| Amino acid | Found | Theory | Amino acid | Found | Theory |
|---|---|---|---|---|---|
| Asx* | 2.82 | 3 | Leu* | 1.06 | 1 |
| Thr | 1.75 | 2 | Tyr | 1.74 | 2 |
| Ser** | 3.29 | 4 | Lys* | 1.10 | 1 |
| Glx* | 1.98 | 2 | His* | 0.95 | 1 |
| Gly | 1.83 | 2 | Arg* | 1.87 | 2 |
| Ala* | 1.11 | 1 | | | |

*Amino acid used for normalization
**No corrections were made for loss during hydrolysis which explains the low value found for Ser.

TABLE 5

Amino acid sequence analysis of glucagon(1-21) purified from yeast strain KFN-31

| Cyclus No. | PTH—amino acid | Yield (pmol) |
|---|---|---|
| 1 | His | 879 |
| 2 | Ser | 427 |
| 3 | Gln | 2321 |
| 4 | Gly | 1343 |
| 5 | Thr | 664 |
| 6 | Phe | 1740 |
| 7 | Thr | 396 |
| 8 | Ser | 176 |
| 9 | Asp | 619 |
| 10 | Tyr | 998 |
| 11 | Ser | 143 |
| 12 | Lys | 570 |
| 13 | Tyr | 751 |
| 14 | Leu | 708 |
| 15 | Asp | 274 |
| 16 | Ser | 70 |
| 17 | Arg | 186 |
| 18 | Arg | 279 |
| 19 | Ala | 423 |
| 20 | Gln | 365 |
| 21 | Asp | 41 |

The average reptitive yield calculated from Gln$_3$ and Gln$_{20}$ was 90%.

We claim:

1. A process for producing glucagon which method comprises
   (1) culturing a transformed *Saccharomyes cerevisiae* host strain which strain contains a replicable expression vector which vector contains the glucagon gene operably linked to a suitable promotor and secretory leader sequence under culturing conditions suitable for secretion of the glucagon polypeptide, and (2) recovering the secreted glucagon polypeptide from the culture medium.

2. A transformed *Saccharomyces cerevisiae* host strain which strain comprises a replicable expression vector, which vector contains the glucagon gene operably linked to a suitable promotor and secretory leader sequence, and which strain is capable of secreting the glucagon polypeptide in recoverable amounts when the strain is cultured under conditions suitable for secretion of the glucagon polypeptide.

* * * * *